United States Patent [19]

Noguchi

[11] Patent Number: 4,805,292
[45] Date of Patent: Feb. 21, 1989

[54] SUTURING NEEDLE WITH SUTURE AND METHOD OF PRODUCING THE SAME

[75] Inventor: Takeshi Noguchi, Osaka, Japan

[73] Assignee: Kabushiki Kaisha Mutec, Osaka, Japan

[21] Appl. No.: 140,779

[22] Filed: Dec. 30, 1987

Related U.S. Application Data

[62] Division of Ser. No. 58,173, Jun. 4, 1987.

[30] Foreign Application Priority Data

Jun. 12, 1986 [JP] Japan .................................. 61-136758
Sep. 22, 1986 [JP] Japan .................................. 61-224664
Nov. 21, 1986 [JP] Japan .................................. 61-279250

[51] Int. Cl.⁴ .................................................. B23P 9/00
[52] U.S. Cl. ........................................ 29/445; 29/517; 29/455.1; 128/339; 163/5
[58] Field of Search ................. 29/516, 517, 455 R, 29/422, 469.5, 445; 128/339; 163/5

[56] References Cited

U.S. PATENT DOCUMENTS

| | | | |
|---|---|---|---|
| 1,591,021 | 7/1926 | Davis | 128/339 |
| 1,844,364 | 2/1932 | Lowrie | 128/339 |
| 2,411,079 | 11/1946 | Baule | 29/517 X |
| 2,795,832 | 6/1957 | Zinke | 29/517 X |
| 2,839,824 | 6/1958 | Berg | 29/417 |
| 3,109,231 | 11/1963 | Johnson | 29/411 |
| 3,716,902 | 2/1973 | Pearce | 29/417 X |
| 3,807,015 | 4/1974 | Steger | 29/445 X |
| 4,054,144 | 10/1977 | Hoffman et al. | 128/339 |
| 4,140,125 | 2/1979 | Smith | 128/339 X |
| 4,672,734 | 6/1987 | Kawada et al. | 128/339 X |

FOREIGN PATENT DOCUMENTS

| | | | |
|---|---|---|---|
| 2905398 | 8/1980 | Fed. Rep. of Germany | 128/339 |
| 1121944 | 7/1968 | United Kingdom | 128/339 |

Primary Examiner—Charlie T. Moon
Attorney, Agent, or Firm—Mason, Fenwick & Lawrence

[57] ABSTRACT

A suturing needle with suture used in a surgical operation and a method of producing the same. The suturing needle is formed of a single or two or more doubled hollow tubes and a core material inserted thereinto, which is fixed to the tip and root of the suturing needle, whereby, when the suturing needle is broken during the operation, broken pieces are not scattered and extraction of each broken piece from a body tissue during operation is facilitated.

12 Claims, 6 Drawing Sheets

SUTURING NEEDLE WITH SUTURE AND METHOD OF PRODUCING THE SAME

This application is a continuation of application Ser. No. 58,173, filed 6/4/87.

BACKGROUND OF THE INVENTION

1. Field of the Invention

The present invention relates to a suturing needle with suture used in a surgical operation and a method of producing the same. More specifically, it relates to the suturing needle with suture formed of a hollow tube and a core material inserted thereinto and its production method. The inner core material inserted into the suturing needle is fixed to its tip and root to prevent broken pieces from scattering when the needle is broken to pieces from a body tissue.

2. Description of the Prior Art

Two types of surgical suturing needle are known when classified roughly. One is an eyed type and the other is an eyeless type.

As the eyed type suturing needle, the one disclosed, for example, in Japanese Utility Model Publication No. Sho 46-12549 (12549/1971) is well known. In this type of suturing needle, a threading hole is provided at the end on its root side. A suture is adapted to be inserted through the threading hole of the needle at operation.

On the other hand, as the eyeless type suturing needle, the one disclosed, for example, in Japanese Patent Publication No. Sho 59-15648 (15648/1984) is well known. In this type of suturing needle, the suture is bound integrally with the suturing needle beforehand at production. When producing the suturing needle, first a prepared hole having a diameter smaller than the suture is opened on the end surface of the needle root. Thereafter, the prepared hole is expanded into a binding hole having the same or larger diameter than the suture. Then the suture is inserted into the binding hole to be bound integrally with the suturing needle by caulking.

Also, as a modified example of the eyeless type, the one disclosed, for example, in Japanese Patent Publication No. 61-103438 (103438/1986) is known. In this type of suturing needle, a groove for the suture is provided generally throughout the whole length of the suturing needle. The portion of suture inserted into the groove is fixed to the suturing needle by caulking and formed as the suturing needle with suture.

However, in the conventional suturing needle, problems mentioned hereinbelow are encountered.

(1) In the first eyed type suturing needle, it is not only troublesome to thread the suture through the threading hole at every operation, but the body tissue is also susceptible to damage during operation, since the suture portion threaded through the threading hole and folded back exceeds a size of the needle.

Also, when the suturing needle is broken for various reasons, broken pieces are scattered and remain in the body tissue. Besides as it is troublesome to extract these broken pieces, the operation may be badly affected.

(2) In the second eyeless type suturing needle, it necessitates a skilled technique to open the prepared hole in the end surface on the root side of the needle having a reduced diameter, or to expand it further to a prescribed size.

Also, during boring the hole, a drill is susceptible to damage, resulting in a high machining cost.

Besides, if the needle is broken during operation, the same inconvenience as mentioned in the eyed type is created.

(3) In a modified example of the second eyeless type, since a flaw due to the groove aforementioned remains generally throughout the whole length of the suturing needle on its surface, the surface can not be finished finely.

Besides, this type of suturing needle is made of a plate material and thus grinding f its tip, lip or the like is insufficient. Therefore, the sharpness (smooth penetration into the tissue) of the needle is deteriorated and becomes impractical.

In addition, when giving heat treatment to harden the suturing needle during production, since the suture fixed to the suturing needle beforehand is susceptible to damage due to a high heat treatment temperature conducted through the groove, it is difficult to increase the hardness and strength by the heat treatment.

BRIEF SUMMARY OF THE INVENTION

It is a first object of the present invention to provide a suturing needle with suture in which a suture does not need to be threaded at every operation and can be easily fixed at production.

It is a second object of the present invention to provide a suturing needle with suture in which, even when the needle is broken during operation, its broken piece can be kept from remaining in a body tissue.

It is a third object of the present invention to provide economically a suturing needle with suture which is sharp and has a smooth and flawless surface.

It is a fourth object of the present invention to provide a suturing needle with suture in which a needle point can be easily formed and given a resistance force against a shock by preventing the surface hardness from increasing more than necessary.

It is a fifth object of the present invention to provide a suturing needle with suture having a suture cutter at the edge on the needle root side It is a sixth object of the present invention to provide a suturing needle with suture capable of attaining the aforementioned objects.

Though these objects can be attained by the component parts, improvements, combinations and operations constituting the present invention, a specific example will be illustrated in the accompanying drawings and the following detailed description.

Meanwhile, changes and modifications relative to the detailed construction are included in the appended claims.

The suturing needle with suture according to the present invention is formed of a hollow tube and an inner core material, one end of which is fixed to the needle point so as not to be exposed from the needle and the other end is fixed to the needle before a suture fixing hole provided at the rear end thereof, to which the tip of the suture is fixed.

The suturing needle with suture according to the present invention is produced in such a manner that one end of the hollow tube of a unit length inserted with the inner core material is tapered off to form the needle point holding one end of said inner core material as a needle body, which is cut into the length of the suturing needle and at the same time, the other end of the needle body on the opposite side of the needle point is formed with the suture fixing hole and processed to fix the other end of the inner core material and to form the suturing needle. The suturing needle fixed with the inner core material is curved in a prescribed shape and the tip of the suture is fixed to the suture fixing hole of the needle.

BRIEF DESCRIPTION OF THE DRAWINGS

FIG. 2 through FIG. 9 show one example of production procedures of a suturing needle with suture according to the present invention wherein

DETAILED DESCRIPTION OF THE PREFERRED EMBODIMENT

FIG. 1 through FIG. 9 of the accompanying drawings show one embodiment of the present invention, wherein a most popular case of a so-called round needle formed of a suturing needle curved in a circular arc is shown.

Figure 1:
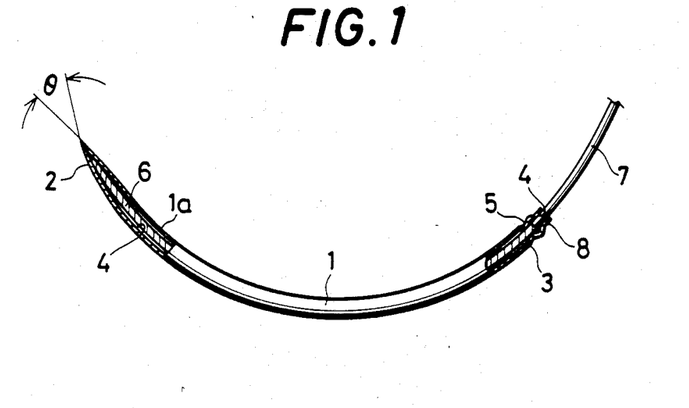
FIG. 1 is a front view showing a needle point and a needle root of a suturing needle with suture according to the present invention in section.

In FIG. 1, the suturing needle 1 is formed of a single hollow tube 1a and a flexible inner core material 6 inserted into a hollow slit 4 thereof.

The inner core material 6 is fixed to a point of the needle 1 at its one end and the other end is fixed with a caulking portion 5 at a root 3 of the needle 1. The point 2 of the suturing needle 1 is formed by welding one end of the hollow tube 1a and one end of the inner core material 6 inserted into the hollow slit 4, fixing by means of pressing or by any other fixing means and swaging the tip portion of the fixed hollow tube 1a and the inner core material 6.

In the hollow slit 4 of the needle root 3, one end of a suture 7 is fixed integrally in abutment with the inner core material 6 by means of caulking or by any other fixing means.

Also, when a body tissue to be sutured is stiff, a sectional shape of the needle 1 is formed such that, for example, generally one third of the total length (needle point) on the needle point side makes a triangle, succeeding portion in the length of about one third (middle) makes a circle and the remaining one third (rear end of the needle) makes an oval.

The needle point 2 is formed with a point angle $\theta$ of a prescribed size at its tip, and an apex of the triangular section at the needle point is formed with a cutter blade.

Meanwhile, when the body tissue to be sutured is soft, a circular shape is more suitable than a square as the sectional shape of the needle point.

Next, production procedures of the suturing needle with suture according to the present invention will be explained (refer to FIG. 2 through FIG. 9).

As the hollow tube which is a material for the needle win this case, stainless steel in the group of SUS 304 of the Japanese Industrial Standard (JIS) is utilized.

Figure 2:
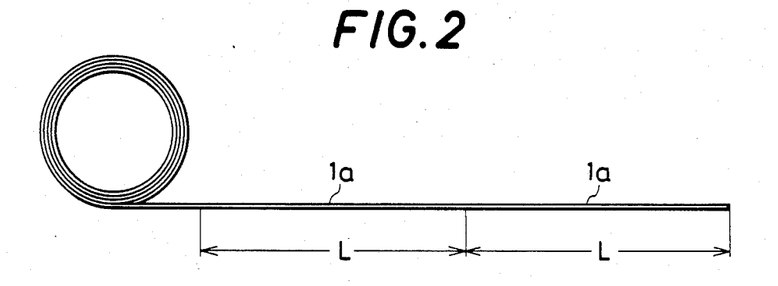
FIG. 2 is a front view showing the state where a rolled hollow tube having a reduced diameter is straightened and cut in a unit length.

(1) After straightening the rolled hollow tube 1a having a reduced diameter, it is cut into a unit length L (refer to FIG. 2).

Figure 3:
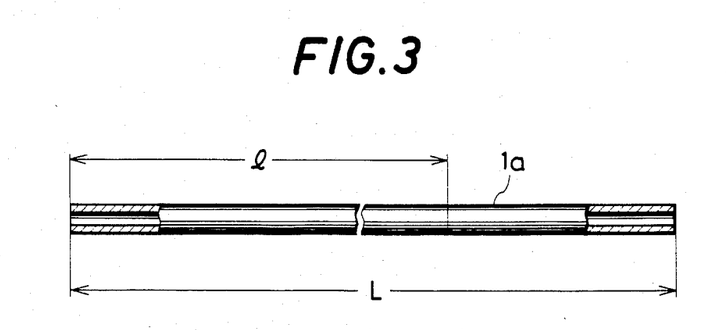
FIG. 3 is a front view showing relationships between the unit length of the cut hollow tube and the length of the suturing needle as a finished product, FIG. 4 a sectional view showing the hollow tube inserted with an inner core material.

The unit length L in this case is, as shown in FIG. 3, decided by taking into account the length 1 (8–50 mm) of the suturing needle as the finished product and the grip length at tip swaging or the like.

Figure 4:
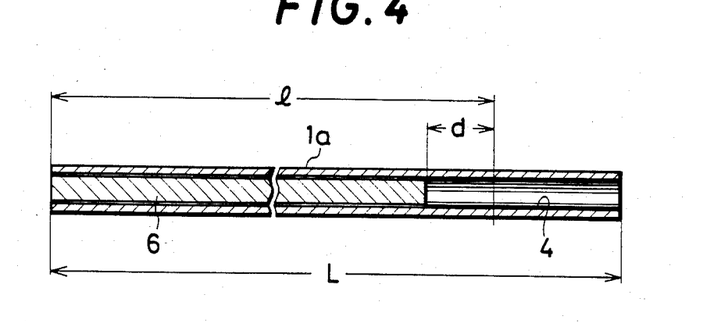

(2) Into the hollow tube 1a-cut into the unit length L, the flexible inner core material 6 having the length shorter by d than the needle length 1 is inserted (refer to FIG. 4).

The length d is decided mainly by taking into account the inserting length of the suture 7 fixed within the hollow slit 4 at the needle root 3 (for example 4–5 mm).

Also, as a material for the inner core material 6, a metal or non-metal different from the hollow tube 1a may be utilized besides stainless steel of SUS 301 or SUS 304 of the same group as the hollow tube 1a.

(3) When the inner core material 6 is formed by the stainless steel SUS 301 or SUS 304 of the same group as the hollow tube 1a, one end of the hollow tube 1a is fixed integrally with the inner core material 6 by means of welding, pressing or any other fixing means.

Figure 5:
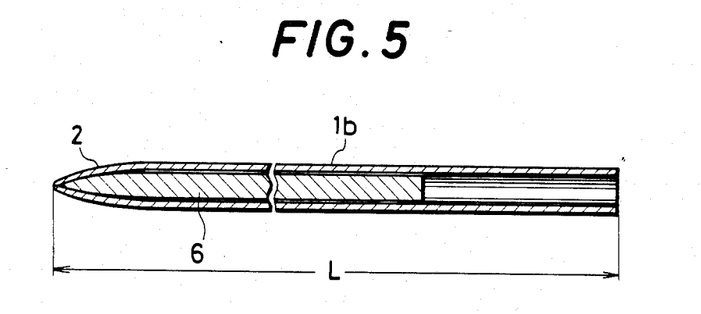
FIG. 5 is a sectional view showing the state where a needle point is formed on the hollow tube to make a needle body.
Figure 6:
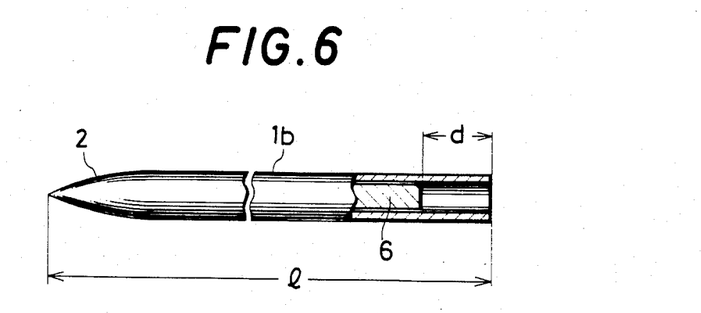
FIG. 6 is a partially sectional front view showing the needle body cut into the length of the suturing needle.

In the next place, the integral portion is swaged at the tip to form the needle point 2, thereby forming the needle body 1b (refer to FIG. 5). In addition, when forming the needle point 2, in order to raise the product value, the inner core material 6 is made so as not to be exposed from the hollow tube 1a. Also, in this case, one end of the inner core material 6 may be made slightly inward from the end surface of the hollow tube 1a to form the needle point 2 by welding, pressing or any other fixing means and swaging.

Figure 10:
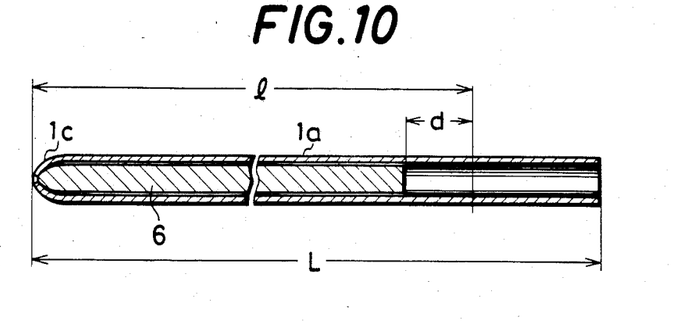
FIG. 10 is a sectional front view corresponding to FIG. 5 showing another embodiment of a suturing needle with suture according to the present invention.

Meanwhile, when the inner core material 6 is made of the metal or non-metal different from the hollow tube 1a, as shown in FIG. 10, one end of the hollow tube 1a is roughly reduced to form a tapered tip 1c. Then, the inner core material 6 having substantially the same shape as the tapered tip 1c is inserted into the hollow tube 1a, which are both swaged at the tips to form the needle point 2, thereby forming the needle body 1b. In addition, similarly to the aforementioned, when forming the needle point 2, the inner core material 6 is made so as not to be exposed from the hollow tube 1a (refer to FIG. 5).

(4) When producing the round needle, a nose shape is formed at the tip by grinding. When producing the square needle, the needle point or about one third of the total length on the needle point side is triangularly pressed to form a cutting edge. The needle point of the needle body 1b formed with the nose and the cutting edge is roughly ground, and the needle body 1b is cut at the position of the needle length l from the needle point (refer to FIG. 6).

Figure 7:
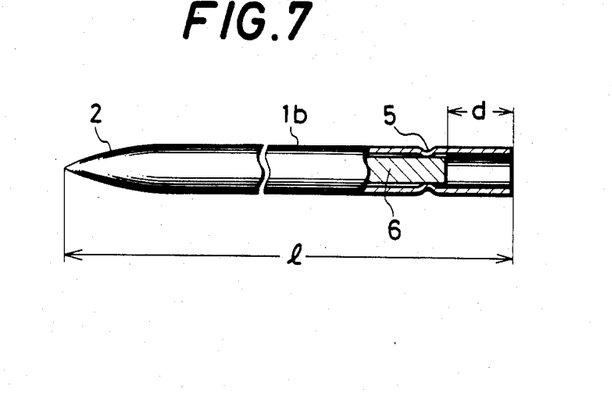
FIG. 7 is a partially sectional front view showing the rear end of the inner core material fixed to the suturing needle.
Figure 8:
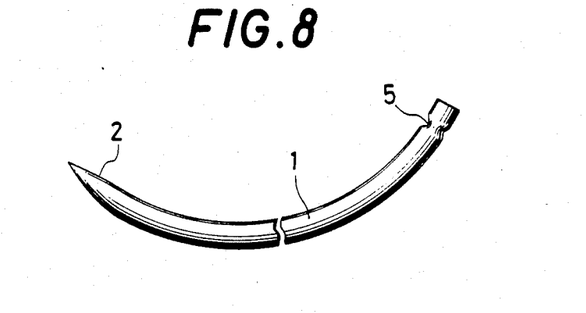
FIG. 8 is a front view showing the suturing needle curved in a prescribed shape.

(5) A periphery of the needle body 1b corresponding to the rear end of the inner core material 6 is caulked to be fixed thereto at the caulked portion 5 (refer to FIG. 7). Moreover, the needle body 1b is pressed and given a curved shape such as the semicircular or ⅜ circular shape to form the needle 1 (refer to FIG. 8). In the meantime, curling of the needle body 1b may be executed before caulking and fixing the rear end of the inner core material 6 aforementioned.

The suturing needle 1 curved in a prescribed shape is heat treated (e.g. at 300° C. for 10 minutes) if necessary to increase its hardness as well as strength.

(6) The suturing needle 1 curved or heat treated is provided with a surface finish such as an electrolytic grinding and washing to remove slight damage caused on the surface during curving or discoloration resulting from the heat treatment. An ultrasonic or fluoride washing may be utilized as the washing.

Figure 9:
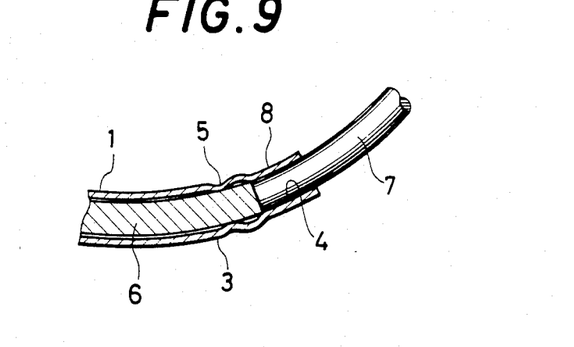
FIG. 9 is a sectional view of the essential portion showing a detailed suture mount of the suturing needle.

(7) The suture 7 is inserted into the hollow slit 4 at the rear end of the needle 1 and fixed with the caulking portion 8 of the needle 1 at the inserted portion (refer to FIG. 9 and FIG. 1).

Figure 14:
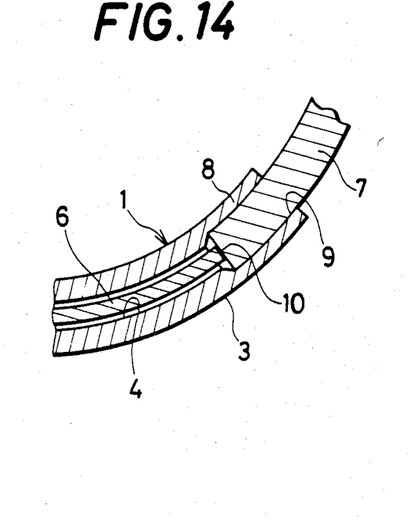
FIG. 14 is a sectional view of the essential portion corresponding to FIG. 9 showing another embodiment of the mount of the inner core material and the suture.
Figure 15:
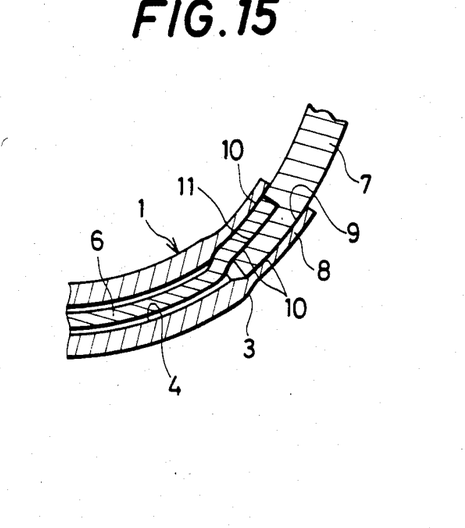
FIG. 15 is a sectional view of the essential portion corresponding to FIG. 9 showing still another embodiment of the mount of the inner core material and the suture.

Meanwhile, the suture 7 may be fixed, as shown in FIG. 14, by expanding the hollow slit 4 to form a suture fixing hole 9 and to adhere the contact surface with the inner core material 6 by means of an adhesive 10, or as shown in FIG. 15, by forming a notched face 11 partly on the side of the suture 7 to overlap the inner core material 6 thereon for caulking, or by using the adhesive 10 together.

The production procedures mentioned heretofore may be employed also in the hollow tube made of a stainless material such as stainless steel in SUS 301 group or titanium besides stainless steel in SUS 304 group as the material of the suturing needle 1. When, however, the material such as silicoroy having a sufficient hardness is used as the material of the needle 1, heat treatment and electrolytic grinding processes among the above production procedures may be omitted.

In this embodiment, since the suturing needle 1 is formed with the hollow tube 10, and at production, a prepared hole for fixing the suture 7 does not require to be opened at the rear end of the needle 1 or further to be expanded, fixing of the suture 7 is considerably simplified.

In addition, into the hollow slit 4 of the needle 1, the inner core material 6 fixed by the needle point 2 and needle root 3 is inserted. Therefore, the needle 1 is not only strengthened by the inner core material 6, but even if the needle 1 is broken for any reason during operation, by pulling a portion of the needle 1 remaining outside the tissue, broken pieces linked together with the inner core material 6 can be easily extracted.

Also, the needle point 2 of the needle 1 is annealed when welding one end of the hollow tube 1a, so that it can be easily formed by tip swaging. Besides, the surface hardness of the needle point 2 thus formed is not increased so excessively as to lose its tenacity, and thus the resistance force against shock is strengthened.

In addition, when forming the needle 1 with the hollow tube 1a, the inner core material 6 can be inserted into the hollow tube 4 of the needle 1 without disposing a groove generally throughout the total length thereof. Therefore, the needle surface is free from any flow caused by the groove and grinding of the nose and cutting edge is performed sufficiently, and thus a sharp suturing needle 1 having a smooth surface can be provided.

In the meantime, since the suture 7 is fixed to the rear end of the needle 1 in the last stage of heat treatment, the suture 7 is not damaged or discolored by the high temperature.

Figure 11:
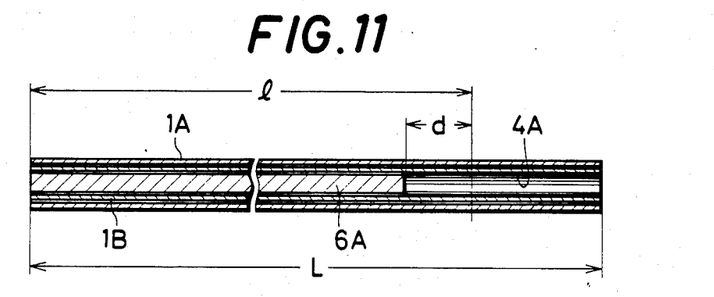
FIG. 11 is a sectional front view corresponding to FIG. 4 showing still another embodiment of a suturing needle with suture according to the present invention.
Figure 12:
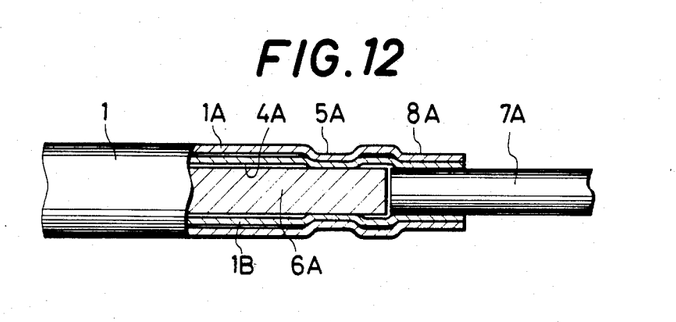
FIG. 12 is a partially sectional front view showing the detailed mount of the inner core material and the suture in the embodiment of FIG. 11.

FIG. 11 and FIG. 12 show another embodiment of the present invention, wherein an inner core material 6A is inserted into a hollow slit 4A formed inside a double hollow tube 1A, 1B doubled via a slight gap, and its rear end and a suture 7A are respectively fixed with a caulking portion 5A and 8A of the double hollow tube 1A, 1B.

When forming the suturing needle 1 in such a manner, in addition to advantages obtained by the embodiment aforementioned, overlapping of poor material portions of the hollow tubes 1A, 1B can be avoided, improving the strength of the suturing needle 1.

Also, if a material used in the inner hollow tube 1B is lower in cost than that of the outer hollow tube 1A, the material cost can be reduced compared with a single tube needle having the same thickness.

Figure 13:
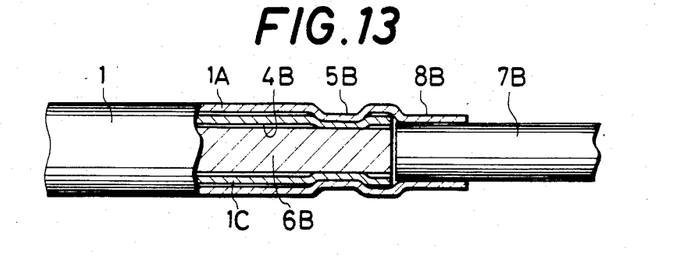
FIG. 13 is a partially sectional front view showing a modified embodiment of FIG. 12.

FIG. 13 shows still another embodiment of the present invention, wherein an inner core material 6B is inserted into a hollow slit 4B formed inside the hollow tubes 1A, 1C having a different length and doubled via a slight gap, and its rear end is fixed with a caulking portion 5B of the hollow tubes 1A, 1C and a suture 7B is fixed with a caulking portion 8B of the outer hollow tube 1A slightly longer than the inner hollow tube 1C.

When the suturing needle 1 is formed in such a manner, in addition to advantages obtained by the embodiment shown in FIG. 11 and FIG. 12, the diameter of the suture 7B fixed to the needle 1 can be enlarged to decrease a difference with the outside diameter of the needle 1. Thus the strength of the suture 7B fixed to the needle 1 having the same size can be strengthened at suturing.

Figure 16:
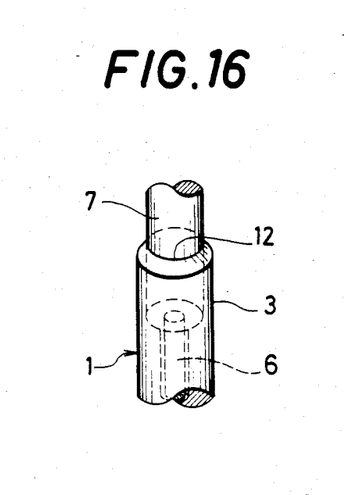
FIG. 16 is a perspective view of the essential portion showing one embodiment in which a suture cutter is formed at the edge on the needle root side of a suturing needle.
Figure 17:
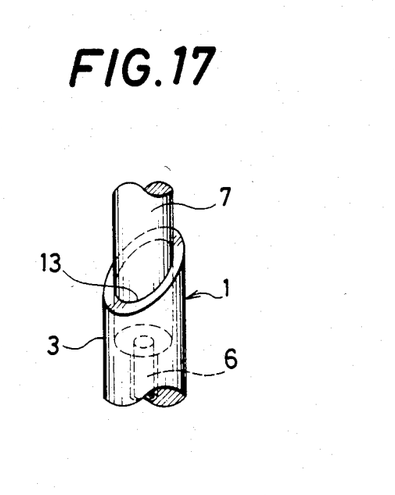
FIG. 17 is a perspective view of the essential portion showing another embodiment in which a suture cutter is formed at the edge on the needle root side.

FIG. 16 and FIG. 17 show another different embodiment of the present invention, wherein a suture cutter 12, 13 is disposed on the needle 1 of each embodiment aforementioned.

That is to say, in FIG. 16, the suture cutter 12 is formed circularly at the edge of the needle root 3 of the needle 1 in a right angle to the lengthwise direction, while in FIG. 17, the suture cutter 13 is formed ovally at the edge formed by cutting the needle root 3 diagonally. Meanwhile, the suture cutter 12, 13 is not limited to these embodiments, but it may be formed in a different shape.

When the suture cutter 12, 13 is disposed at the edge of the needle root 3, during suturing operation or after operation, if the needle 1 is turned in a direction normal to the suture 7 while stretching it, the suture 7 may be easily cut with the cutter 12, 13 without using scissors.

In the meantime, in each embodiment mentioned above, the suturing needle 1 formed by the hollow tube 1a cut into the unit length L and inserted with the inner core material 6 slightly shorter than its length is explained.

The suturing needle 1, however, may be formed by the same production procedures aforementioned in such a manner that, the hollow tube 1a having a reduced diameter is cut, for example, into a long piece of 1-3 m, whose hollow slit 4 is inserted with the inner core material 6 having the same length and cut into the unit length L together.

Figure 18:
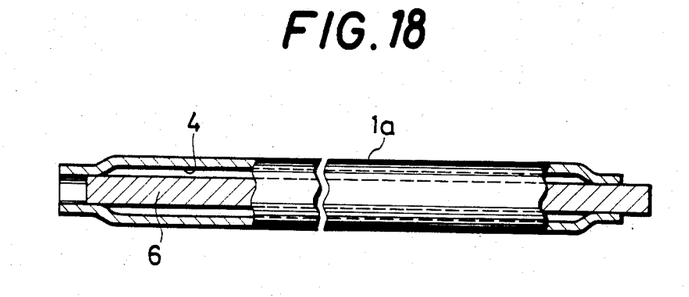
FIG. 18 is a partially sectional front view showing form of needle point when a suturing needle is produced by the other method.

In this case, since opposite ends of the hollow tube 1a having the unit length L hold both ends of the inner core material 6 lightly by the biassing force at cutting, the needle point can be formed by swaging one end of the hollow tube 1a as it is. However, as shown in FIG. 18, by applying the biassing forth to one end of the inner core material 6 in this state, and after moving said one end slightly inward from the end surface thereof, swaging one end of the hollow tube 1a at this portion, the needle point can be formed efficiently. Then, when the other end of the hollow tube 1a is cut into the needle length and the suture is fixed to the suture fixing hole provided at the needle root on the other end, the suturing needle with suture is formed.

Figure 19:
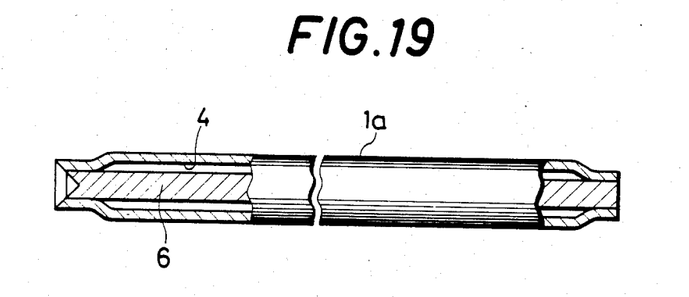
FIG. 19 is a partially sectional view showing another embodiment of FIG. 18.

However, in place of indenting the inner core material 6, as shown in FIG. 19, one end of the hollow tube 1a may be bored conically. Then one end of the inner core material 6 gets slightly inside the end surface of the hollow tube 1a, and thus by swaging the same, the needle point from which the inner core material 6 is not exposed can be easily formed.

When producing the suturing needle by cutting into the unit length after inserting the inner core material into the long hollow tube in such a manner, the needle can be produced with less trouble compared with the case where the inner core material is inserted into the hollow tube cut into the unit length in advance.

In the meantime, specific embodiments explained in the detailed description of the present invention are for illustrative purposes of clarifying the present technique. Therefore, it is to be understood that the present invention is not limited only to the specific embodiments aforementioned and construed narrowly, but rather to be construed broadly that various changes and modifications may be made without departing from the spirit of the present invention and the scope of the appended claims.

What is claimed is:

1. A method of producing a suturing needle with suture characterized in that, inserting an inner core material in
   one end of a hollow tube having a unit length inwardly deforming said one end of said hollow tube and core therein to form a tapered point holding one end of the inner core material to produce a needle body,
   cutting said needle body into the needle length and forming a suture fixing hole on the other end of the needle body opposite the needle point,
   processing the other end of said needle body to fix the other end of the inner core material therein and to form the needle,
   bending said needle fixed with the inner core material therein to a curve of a prescribed shape, and
   fixing a tip of a suture of in the suture fixing hole of the needle.

2. A method of producing a suturing needle with suture in accordance with claim 1, wherein one end of the hollow tube is swaged to form the needle point.

3. A method of producing a suturing needle with suture in accordance with claim 1, wherein the fixing processing is caulking.

4. A method of producing a suturing needle with suture in accordance with claim 1, wherein the needle fixed with the inner core material is given a heat treatment to be hardened to a required value after being curved into a prescribed shape.

5. A method of producing a suturing needle with suture in accordance with claim 1, wherein a suture fixing hole of the needle is formed by slightly expanding a hollow slit at the other end of the hollow tube.

6. A method of producing a suturing needle with suture in accordance with claim 1, wherein before cutting a long hollow tube into a unit length, the inner core material is inserted into said hollow tube.

7. A method of producing a suturing needle with suture in accordance with claim 1, wherein after cutting a long hollow tube into a unit length, the inner core material is inserted into said hollow tube.

8. A method of producing a suturing needle with suture in accordance with claim 1, wherein the needle point is formed after integrally fixing one end of the hollow tube and the inner core material by welding.

9. A method of producing a suturing needle with suture in accordance with claim 2, wherein the needle point is formed after integrally fixing one end of the hollow tube and the inner core material by welding.

10. A method of producing a suturing needle with sutures in accordance with claim 1, wherein after moving one end of the inner core material slightly inside from the edge of the hollow tube, said one end is fixed so as not to be exposed by the hollow tube.

11. A method of producing a suturing needle with suture in accordance with claim 6, wherein after moving one end of the inner core material slightly inside from the edge of the hollow tube, said one end is fixed so as not to be exposed by the hollow tube.

12. A method of producing a suturing needle with suture in accordance with claim 7 wherein after moving one end of the inner core material slightly inside form the edge of the hollow tube, said one end is fixed so as not to be exposed by the hollow tube.

* * * * *